(12) United States Patent
Enders et al.

(10) Patent No.: US 9,606,132 B2
(45) Date of Patent: Mar. 28, 2017

(54) METHODS OF MONITORING ADHERENCE TO LURASIDONE THERAPY

(71) Applicant: Ameritox, Ltd., Baltimore, MD (US)

(72) Inventors: Jeffrey Enders, High Point, NC (US); Erin Strickland, Greensboro, NC (US); Gregory L. McIntire, Greensboro, NC (US); Ayodele Morris, Midland, TX (US)

(73) Assignee: AMERITOX, LTD., Baltimore, MD (US)

( * ) Notice: Subject to any disclaimer, the term of this patent is extended or adjusted under 35 U.S.C. 154(b) by 145 days.

(21) Appl. No.: 14/567,935

(22) Filed: Dec. 11, 2014

(65) Prior Publication Data

US 2015/0168431 A1    Jun. 18, 2015

Related U.S. Application Data

(60) Provisional application No. 61/915,070, filed on Dec. 12, 2013, provisional application No. 62/035,821, filed on Aug. 11, 2014.

(51) Int. Cl.
*G01N 33/94*    (2006.01)
*H01J 49/00*    (2006.01)

(52) U.S. Cl.
CPC ......... *G01N 33/94* (2013.01); *G01N 2560/00* (2013.01); *G01N 2800/52* (2013.01)

(58) Field of Classification Search
CPC ................................. G01N 33/94; H01J 49/00
USPC ........................ 250/282; 436/91–92, 96, 173
See application file for complete search history.

(56) References Cited

U.S. PATENT DOCUMENTS

2014/0113912 A1*  4/2014  Loebel ................. A61K 31/496
                                              514/254.04
2015/0175596 A1*  6/2015  Veerappan ........... C07D 417/12
                                              544/368

OTHER PUBLICATIONS

Hiemke, C. et al, Theraputic drug monitoring 2004, 26, 156-160.*
Neef, C. et al, Pharmaceutical Medicine 2008, 22, 235-244.*
Adaway, J. E. et al, Journal of Chromatography B 2012, 883-884, 33-49.*
Saar, E. et al, Drug Testing and Analysis 2012, 4, 376-394.*
Patteet, L. P. et al, Therapeutic Drug Monitoring 2012, 34, 629-651.*
Koo, T.-S. et al, Biomedical Chromatography 2011, 25, 1389-1394.*
Baselt, R.C., "Disposition of Toxic Drugs and Chemicals in Man," 10th edition, Biomedical Publications. p. 1179 (2014).
Caccia, Silvio et al., "Critical appraisal of lurasidone in the management of schizophrenia," Neuropsychiatric Disease and Treatment. 8:155-168(2012).
Center for Drug Evaluation and Research. Application No. 200603, Lurasidone hydrochloride, Dec. 30, 2009.
Citrome, L., "Lurasidone for schizophrenia: a review of the efficacy and safety profile for this newly approved second-generation antipsychotic," The International Journal of Clinical Practice. 65, 2, 189-210 (2010).
Kyeong-Ryoon, Lee et al., "Pharmacokinetics of lurasidone, a novel atypical anti-psychotic drug, in rats," Xenobiotica. 41(12):1100-1107 (2011).
Risbood, Veneeta et al., "Lurasidone: An Atypical Antipsychotic for Schizophrenia," The Annals of Pharmacotherapy. 46:1033-1046 (2012).
Yoon-Jee, Chae et al., "A Sensitive and Selective LC-MS Method for the Determination of Lurasidone in Rat Plasma, Bile, and Urine," Chromatographia. 75:1117-1128 (2012).

* cited by examiner

*Primary Examiner* — Arlen Soderquist
(74) *Attorney, Agent, or Firm* — Perkins Coie LLP

(57) ABSTRACT

The present disclosure provides methods for monitoring subject (e.g., patient) adherence to lurasidone therapy, for example as a component of treating a subject for a mental health disorder such as schizophrenia.

17 Claims, 1 Drawing Sheet

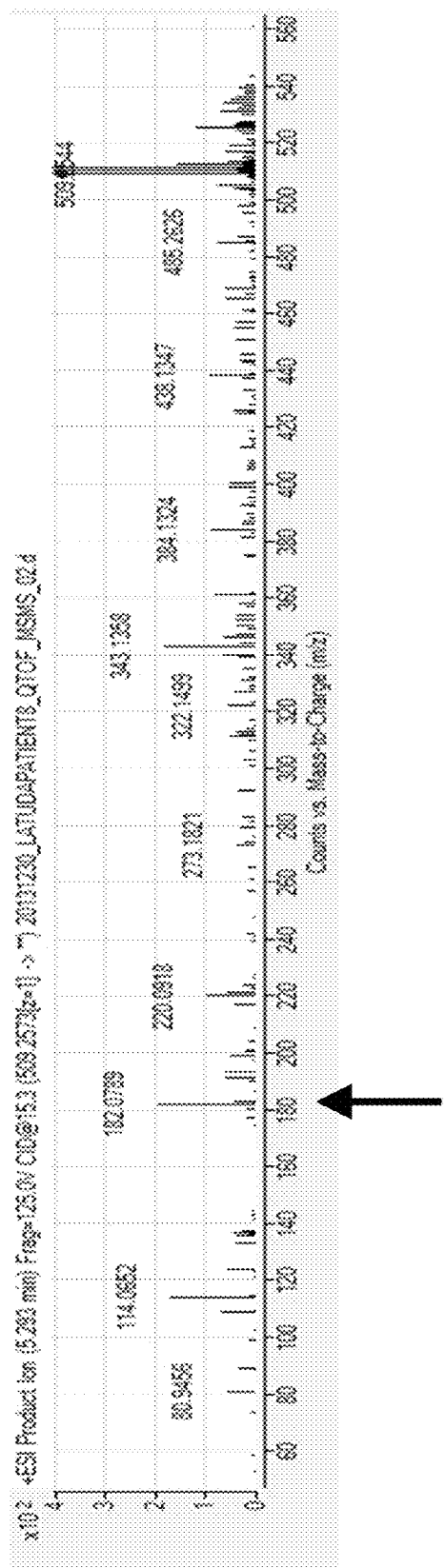

METHODS OF MONITORING ADHERENCE TO LURASIDONE THERAPY

PRIORITY CLAIM

This application claims priority to U.S. Provisional Patent Application Ser. No. 61/915,070, filed Dec. 12, 2013, and to U.S. Provisional Patent Application Ser. No. 62/035,821, filed Aug. 11, 2014, the entire contents of each of which are incorporated herein by reference and relied upon.

TECHNICAL FIELD

The present disclosure provides methods for monitoring subject (e.g., patient) adherence to lurasidone therapy, for example as a component of treating a subject for a mental health disorder such as schizophrenia.

BACKGROUND

Lurasidone (Latuda®) is an atypical antipsychotic prescribed for the treatment of acute symptoms of schizophrenia. Drug adherence has been shown to be particularly low in patients with schizophrenia. Urine drug testing has been employed by behavioral health clinicians to monitor patient compliance through analysis of drugs and their major metabolites. Typically, adherence to lurasidone therapy is monitored by evaluating levels of lurasidone and one of its plasma metabolites, M11 (2-{(3,5-Dioxo-4-azatricyclo[5.2.1.0$^{2,6}$]dec-4-yl)methyl}cyclohexanecarboxylic acid) (see Table 1 for structure). However, these molecules are present in only low levels after dosing, thus false negative monitoring results are common. Such false negative reports can improperly induce a clinician (e.g., a physician or psychiatrist) to alter a compliant subject's lurasidone therapeutic regimen when no alteration is warranted. Improved methods for assessing and monitoring a subject's adherence to lurasidone therapy are needed.

SUMMARY

The present disclosure provides methods for monitoring patient adherence to lurasidone therapy, for example as a component of treating a subject for a mental health disorder such as schizophrenia.

In one embodiment, the present disclosure provides a method for monitoring lurasidone therapy in a subject who has been prescribed lurasidone therapy, the method comprising: obtaining a fluid sample from a subject who has been prescribed lurasidone therapy, analyzing the fluid sample for the presence of M8/M9, M21, and M22, and identifying the subject as adherent to the prescribed lurasidone therapy if the fluid sample contains M8/M9, M21, or M22 above a threshold level but non-adherent if the fluid sample contains no M8/M9, M21, or M22 or an amount of M8/M9, M21, or M22 below a threshold level.

In another embodiment, the present disclosure provides a method of evaluating compliance with lurasidone therapy in a subject, the method comprising obtaining a fluid sample (e.g., urine) from the subject, analyzing the fluid sample for presence or absence of an analyte, and identifying the subject as compliant if the analyte is present in the fluid sample.

BRIEF DESCRIPTION OF THE FIGURES

FIG. 1 shows the MS/MS spectra of M8/M9 metabolite of lurasidone.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

Lurasidone (Latuda®) is an atypical antipsychotic prescribed for the treatment of acute symptoms of schizophrenia. Lurasidone has a molecular weight of 492.6 g/mol, and empirical formula of $C_{28}H_{36}N_4O_2S$, a $pK_a$ of 7.6, a log P of 5.9, a CAS number of 367514-87-2, a mass-to-charge ratio (m/z) of 493.6 when ionized with addition of a proton (ESI MS), and has a formula chosen from the stereoisomeric Formulas (I) and (II) shown below:

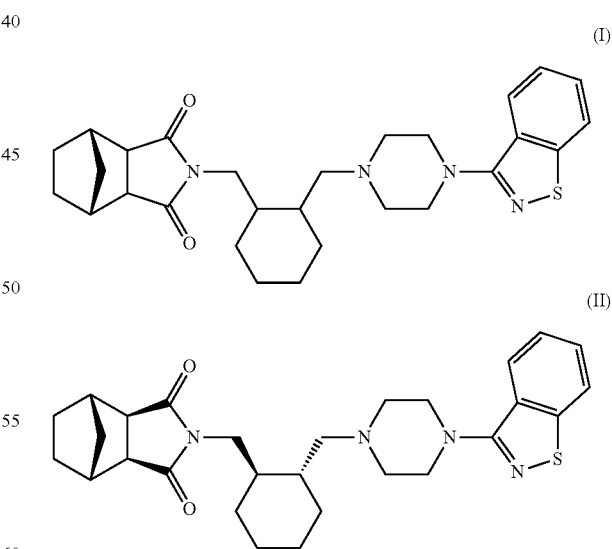

Lurasidone is commercially available as 20 mg, 40 mg, 60 mg, 80 mg, and 120 mg tablets and is typically prescribed or administered at 40 or 80 mg per day. It is absorbed after oral administration with a bioavailability of 9 to 19%. Dosing is designed to be with food as this can increase the bioavailability by 100%. The mean elimination half-life is 18 hours.

Steady state serum concentrations for Lurasidone are typically achieved after 7 days of dosing.

Lurasidone is metabolized in the liver primarily by CYP3A4. Metabolism includes oxidative N-dealkylation, hydroxylation of the norbane ring, S-oxidation, and reductive cleavage of the isothiazole ring followed by S-methylation. Nearly two dozen metabolites of lurasidone have been previously identified. Select metabolites of lurasidone are shown in Table 1 below.

TABLE 1

Select Metabolites of Lurasidone.

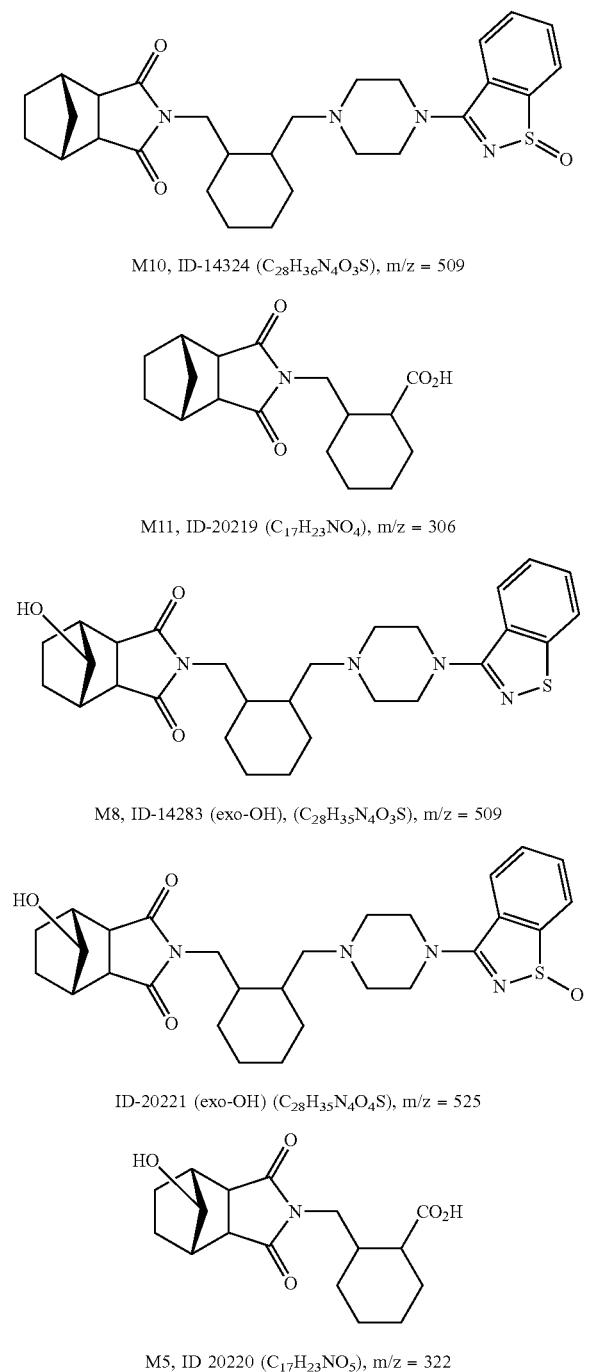

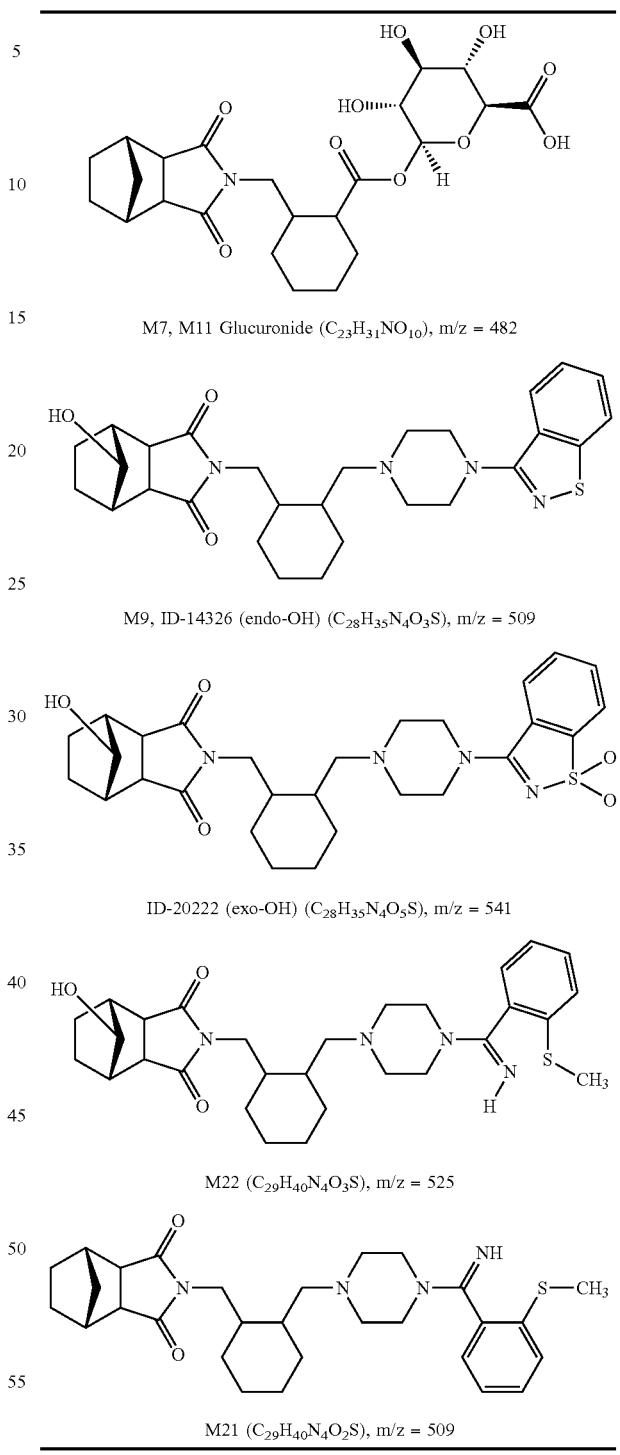

Among the various known lurasidone metabolites, M11 and M5 are not biologically active, but have been reported to be "major" metabolites (e.g., defined by ≥10% total drug exposure). Metabolites ID-14283 (M8) and ID-14326 (M9) are known to be biologically active, but not considered "major" metabolites.

Lurasidone metabolite designated M8 and its isomer M9 ($C_{28}H_{36}N_4O_3S$) are a result of the hydroxylation of the norborane ring and are both the only known active metabolites of lurasidone. Previous studies using radiolabelled lurasidone (e.g., [carbonyl-$^{14}$C]lurasidone) have identified M8 (ID-14283) as present in an unspecified low amount in serum of humans after (40 mg oral dosing) and in mice, rats, dogs, and monkeys after 10 mg/kg oral administration. Additionally, M9 (ID-14326) was also identified in rats and dogs, and was the more preferential metabolite in dogs over M8.

Lurasidone metabolite designated M21 ($C_{29}H_{40}N_4O_2S$) is the result of reductive opening of the isothiazole ring followed by methylation of the free sulfur. Previous studies using radiolabelled lurasidone (e.g., [carbonyl-$^{14}$C]lurasidone) did not detect M21 as a circulating metabolite in serum of any of the animal models. However, other metabolites that have been further modified from the original M21 compound (N-dealkyl-M21, Keto-N-dealkyl M21, and Tri-oxy-M21) have been identified in the majority of the animal models in unspecified low amounts in serum, including humans.

Lurasidone metabolite designated M22 ($C_{29}H_{40}N_4O_3S$) is the result of reductive opening of the isothiazole ring followed by methylation of the free sulfur and hydroxylation of the norborane ring. Previous studies using radiolabelled lurasidone (e.g., [carbonyl-$^{14}$C]lurasidone) have identified M22 as present in an unspecified low amount in serum of humans (after 40 mg oral dosing) and in mice, rats and dogs after 10 mg/kg oral administration. However, M22 was present in humans at less than 10% of the total drug-related exposure, and was not detected in any amount in other animal models, such as rabbits or monkeys. Previous studies do not identify M22 as a primary circulating metabolite in mice, rats, rabbits, dogs, monkeys or humans.

Drug adherence has been shown to be particularly low in patients with schizophrenia. Urine drug testing has been employed by behavioral health clinicians to monitor patient compliance through analysis of drugs and their major metabolites.

In one embodiment, the present disclosure provides a method for monitoring lurasidone therapy in a subject. In some embodiments, the method comprises obtaining a fluid sample from a subject who has been prescribed lurasidone therapy, analyzing the fluid sample for the presence of M8/M9, M21, and M22, and identifying the subject as adherent to the prescribed lurasidone therapy if the fluid sample contains M8/M9, M21, and/or M22 above a threshold level but non-adherent if the fluid sample contains no M8/M9, M21, and/or M22 or an amount of M8/M9, M21, and/or M22 below a threshold level. In some embodiments, the method further comprises identifying the subject as having been prescribed lurasidone therapy. In some embodiments, the method further comprises counseling the subject on dangers of non-adherence to lurasidone therapy if the subject is identified as non-adherent. In some embodiments, the threshold level is a minimum detectable amount of M8/M9, M21, and/or M22. In some embodiments, the threshold level is about 5 ng/mL to about 500 ng/mL, for example about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 125 ng/mL, about 150 ng/mL, about 175 ng/mL, about 200 ng/mL, about 225 ng/mL, about 250 ng/mL, about 275 ng/mL, about 300 ng/mL, about 325 ng/mL, about 350 ng/mL, about 375 ng/mL, about 400 ng/mL, about 425 ng/mL, about 450 ng/mL, about 475 ng/mL, or about 500 ng/mL. In some embodiments, the threshold level is about 50 ng/mL. In some embodiments, the fluid sample is a urine sample.

In another embodiment, the present disclosure provides a method of evaluating compliance with lurasidone therapy in a subject. In some embodiments, the method comprises obtaining a fluid sample from a subject who has been prescribed lurasidone therapy, analyzing the fluid sample for presence or absence of an analyte, and identifying the subject as compliant if the analyte is present in the fluid sample. In some embodiments, the analyte comprises lurasidone and/or a lurasidone metabolite. In some embodiments, the analyte is selected from the group consisting of M5, M10, M11, M11 Glucuronide, ID-20221, ID-20222, M8/M9, M21, and M22, or a combination thereof. In some embodiments, the analyte comprises M8/M9, M21, and/or M22. In some embodiments, the analyte is considered present in the fluid sample if the analyte is detected above a threshold value. In some embodiments, the threshold value is about 50 ng/mL. In some embodiments, the threshold value is about 5 ng/mL. In some embodiments, the method further comprises identifying the subject as having been prescribed lurasidone therapy.

In some embodiments, two or more drug metabolites (e.g., primary, secondary, and/or tertiary metabolites) are determined, a ratio of one metabolite to at least one other metabolite is calculated, and a risk of the subject's noncompliance is determined if the ratio falls outside confidence intervals or mathematically transformed and normalized range of that ratio for the daily dose of the drug. In some embodiments, one metabolite is the parent drug originally dosed to the patient. In some embodiments, the ratio is of one metabolite to the sum of all metabolites.

EXAMPLES

Example 1

Urine samples of normally metabolizing human subjects who were known to be taking chronic doses of lurasidone were tested for the presence of lurasidone and eleven metabolites (excluding isomeric metabolites). Each patient sample was analyzed twice to ensure accuracy. Due to the high probability for false identification of isobars, MS/MS data was collected and selectively looked at to add confidence to the identification. In particular, it was determined that a peak that could have arisen from any of M8, M9 or M10 was actually M8/M9 (stereoisomers) because of the presence of a peak at 182 m/z indicating a hydroxylated norborane ring. If the peak had been M10, there would have been a prominent peak at 166 m/z indicating an un-hydroxylated norborane ring and a peak at 152 m/z indicating an oxidation on the sulfur and neither peak was observed. The 182 m/z peak is highlighted in FIG. 1 (arrow) indicating that the species identified is M8/M9. It is also clear in this spectrum that there are not any apparent peaks between 140-170 m/z where the expected M10 fragments of 166 and 152 m/z would appear indicating that the M10 is not present at any significant amount. Due to the high mass accuracy and low mass error on the Quadrupole Time-of-Flight (Q-ToF) Mass Spectrometer, compounds that have similar mass to charge ratios (e.g., m/z), but different chemical formulas were differentiated with the searching algorithm (e.g., M8/M9 and M21).

In plasma, lurasidone has been reported to account for 12% of the total radioactivity post oral dosing, while ID-20219 (M11) represents 24% of the total radioactivity, and ID-20220 (M5) for at least 10% (e.g., about 11%) of the total radioactive dose in the plasma. Excretion studies in humans report that the drug is excreted with 80% in the feces and 9% recovered in the urine.

Surprisingly, neither metabolite ID-20220 (M5) nor metabolite ID-20219 (M11) were found to be excreted through human urine in detectable amounts. Instead, the identity of detectable lurasidone metabolites varies widely from subject to subject, as shown in Table 2 below. Only the eight most significant metabolites out of the eleven searched are presented in Table 2 for simplicity.

TABLE 2

Lurasidone Metabolite Distribution in Human Urine

| Subject ID | Run | Lurasidone 492.2559 | M8/M9/M10 508.2508 | M11 305.1627 | M11 Gluc 481.1948 | ID-20221 MW 524.2457 | ID-20222 540.2406 | M22 524.2821 | M21 508.2872 | M4/M5/M6 321.1576 |
|---|---|---|---|---|---|---|---|---|---|---|
| Subject 1 | 1 | ✓^ | ✓* | ✓ | | | | ✓* | ✓* | |
| | 2 | ✓ | ✓* | ✓ | | | | ✓* | ✓* | |
| Subject 2 | 1 | ✓* | ✓* | | | | | ✓* | ✓ | ✓ |
| | 2 | ✓* | ✓* | | | | | ✓* | ✓ | ✓ |
| Subject 3 | 1 | ✓ | ✓ | | ✓* | ✓ | | ✓* | ✓* | |
| | 2 | ✓ | ✓* | | ✓* | ✓ | | ✓* | ✓ | |
| Subject 4 | 1 | | ✓* | ✓* | ✓ | | ✓ | ✓* | ✓ | ✓ |
| | 2 | | ✓* | ✓* | ✓ | | | ✓* | ✓ | ✓ |
| Subject 5 | 1 | ✓* | ✓* | | | | ✓ | ✓* | ✓ | ✓ |
| | 2 | ✓* | ✓* | | | | ✓ | ✓* | ✓ | ✓ |
| Subject 6 | 1 | ✓* | ✓ | ✓ | | | ✓ | ✓* | ✓* | |
| | 2 | ✓* | ✓ | ✓ | | | ✓ | ✓* | ✓* | |
| Subject 7 | 1 | ✓* | ✓* | | | ✓ | ✓ | ✓ | ✓* | ✓ |
| | 2 | ✓* | ✓* | | | ✓ | ✓ | ✓ | ✓* | ✓ |
| Subject 8 | 1 | ✓* | ✓* | ✓ | | | ✓ | ✓ | ✓* | |
| | 2 | ✓* | ✓* | ✓ | | | ✓ | ✓ | ✓* | |
| Subject 9 | 1 | ✓ | ✓ | | | ✓* | | ✓* | ✓* | |
| | 2 | ✓ | ✓ | | | ✓* | | ✓* | ✓* | |
| Subject 10 | 1 | ✓ | ✓ | ✓ | | ✓ | | ✓* | ✓* | ✓* |
| | 2 | ✓ | ✓ | ✓ | | | ✓* | ✓ | ✓* | ✓* |
| Subject 12 | 1 | ✓ | ✓* | | | | | ✓* | ✓* | |
| | 2 | ✓ | ✓* | | | | | ✓* | ✓* | |
| Subject 13 | 1 | ✓ | ✓* | | ✓ | | | ✓* | ✓* | ✓ |
| | 2 | ✓ | ✓* | | ✓ | | | ✓* | ✓* | ✓ |

✓ Indicates that the compound was successfully identified in a qualitative manner;
"^" Indicates that the noted compound was one of the three most abundant compounds identified in that particular sample;
"*" Indicates that the noted compound was one of the three most confidently identified in that particular sample and run.

As shown above, metabolites M8/M9, M21, and M22 were unexpectedly present in detectable quantities in each test of each subject's urine sample. This was unexpected because M8/M9, M21, and M22 are reported to be only minor metabolites detectable in plasma in only a few species. Notably, reliance on the presence of any metabolite other than M8/M9, M21, or M22 in urine would have generated false negative test results for at least half of the 12 subjects listed in Table 2. While lurasidone was detected in the majority of the samples, it was typically not one of the three most abundant peaks in the sample and was unobserved in one sample. Therefore, the monitoring of the M8/M9, M21, and M22 metabolites can be used to reduce the possibility of false negatives.

Example 2

The urine of 20 patients who were prescribed 20 mg of Latuda® (lurasidone) was tested for compliance over 5 days (Table 3). The preponderance of M8/M9, M21, and M22 in the urine as the major metabolic urine compounds is shown in Table 3. Assuming 60 opportunities to determine the patient to be either positive or negative for Latuda® dosing, the use of M8/M9, M21, and M22 resulted in 100% correct identification of those taking the prescribed medicine. The data in Table 4 demonstrate the "normal" nature of the sample validity criteria (i.e., pH, specific gravity, and creatinine). Without the M8/M9, M21, or M22 metabolites, only ~88% were determined to be positive solely by the parent compound lurasidone. Thus, use of M8/M9, M21, and M22 as a urine biomarker at this low dose adds value to compliance monitoring for Latuda®.

TABLE 3

Test Results from Patients Prescribed 20 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| A | 1 | 7.7 | 76.0 | 1.007 | 12.0 | 29.6 | 32.6 | 42.6 |
| | 4 | 7.5 | 163.0 | 1.011 | 149.0 | 456.1 | 240.9 | 76.8 |
| | 5 | 9.0‡ | 134.7 | 1.003 | 9.6 | 21.9 | 21.0 | 40.2 |
| B | 1 | 8.6 | 78.0 | 1.005 | 9.7 | 12.2 | 22.3 | 18.6 |
| | 4 | 5.4 | 121.0 | 1.014 | 14.3 | 15.9 | 104.1 | 33.5 |
| | 5 | 8.4 | 110.6 | 1.006 | 8.8 | 24.7 | 127.9 | 108.7 |

TABLE 3-continued

Test Results from Patients Prescribed 20 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| C | 1 | 5.4 | 287.5 | 1.022 | 12.7 | 38.2 | 201.6 | 153.0 |
|   | 4 | 5.3 | 300.3 | 1.022 | 18.9 | 53.8 | 355.2 | 256.3 |
|   | 5 | 6.5 | 178.3 | 1.014 | 13.2 | 31.4 | 142.1 | 109.1 |
| D | 1 | 6.2 | 193.4 | 1.017 | 9.0 | 11.8 | 118.8 | 57.7 |
|   | 4 | 5.6 | 74.2 | 1.009 | 4.8** | 18.2 | 113.4 | 60.3 |
|   | 5 | 5.6 | 206.9 | 1.017 | 24.4 | 76.0 | 324.0 | 157.3 |
| E | 1 | 7.1 | 95.3 | 1.008 | 33.1 | 70.0 | 88.8 | 43.7 |
|   | 4 | 6.8 | 39.0 | 1.004 | 14.0 | 41.9 | 37.2 | 22.6 |
|   | 5 | 6.3 | 62.1 | 1.007 | 26.2 | 47.0 | 51.9 | 24.4 |
| F | 1 | 6.6 | 225.4 | 1.018 | 24.6 | 82.1 | 81.3 | 46.8 |
|   | 4 | 7.9 | 56.6 | 1.005 | 5.7 | 10.9 | 25.2 | 7.3 |
|   | 5 | 5.5 | 129.8 | 1.016 | 20.3 | 29.6 | 66.7 | 20.4 |
| G | 1 | 6.2 | 22.7 | 1.003 | 6.9 | 8.3 | 44.0 | 7.8 |
|   | 4 | 5.5 | 12.1‡ | 1.002 | 4.7* ** | 6.1 | 17.5 | 4.1** |
|   | 5 | 5.1 | 13.6‡ | 1.003 | 6.5 | 6.7 | 25.1 | 5.3 |
| H | 1 | 6.9 | 171.1 | 1.013 | 6.0 | 6.3 | 53.1 | 16.4 |
|   | 4 | 5.0 | 71.4 | 1.008 | 7.0 | 11.0 | 57.1 | 13.3 |
|   | 5 | 7.1 | 151.0 | 1.009 | 6.6 | 85.7 | 138.4 | 39.5 |
| I | 1 | 5.3 | 24.0 | 1.003 | 4.4* ** | 3.7* ** | 35.3 | 6.1 |
|   | 4 | 5.9 | 27.5 | 1.003 | 2.9* ** | 3.3* ** | 32.5 | 4.4** |
|   | 5 | 4.7 | 22.2 | 1.003 | 6.0 | 7.1 | 29.4 | 4.1** |
| J | 1 | 6.4 | 71.8 | 1.005 | 9.1 | 17.0 | 53.4 | 16.0 |
|   | 4 | 5.0 | 247.5 | 1.018 | 31.3 | 63.7 | 245.2 | 61.0 |
|   | 5 | 5.7 | 120.0 | 1.009 | 18.6 | 38.9 | 134.2 | 34.7 |
| K | 1 | 8.8 | 188.8 | 0.982‡ | 9.1 | 184.5 | 311.8 | 342.0 |
|   | 4 | 8.4 | 65.2 | 0.993‡ | 13.0 | 75.2 | 163.1 | 91.5 |
|   | 5 | 8.4 | 89.0 | 0.993‡ | 12.1 | 97.5 | 221.7 | 107.9 |
| L | 1 | 7.3 | 72.6 | 1.006 | 10.1 | 17.3 | 11.0 | 16.2 |
|   | 4 | 7.8 | 105.3 | 1.004 | 7.3 | 1.2** | 15.8 | 20.9 |
|   | 5 | 8.0 | 87.1 | 1.006 | 13.6 | 32.2 | 21.7 | 27.8 |
| N | 1 | 6.6 | 210.0 | 1.002 | 5.7 | 11.0 | 14.9 | 8.4 |
|   | 4 | 6.5 | 113.1 | 1.009 | 24.3 | 38.9 | 111.0 | 51.1 |
|   | 5 | 6.5 | 13.3‡ | 1.001‡ | 5.4 | 4.3** | 10.7 | 5.0 |
| O | 1 | 7.1 | 94.7 | 1.010 | 7.8 | 8.6 | 49.5 | 19.0 |
|   | 4 | 7.8 | 46.5 | 1.005 | 4.3** | 2.8** | 15.6 | 6.9 |
|   | 5 | 5.7 | 119.3 | 1.010 | 10.2 | 18.1 | 53.8 | 16.2 |
| P | 1 | 8.1 | 153.8 | 1.008 | 12.9 | 41.4 | 92.2 | 46.0 |
|   | 4 | 8.2 | 196.9 | 1.005 | 12.5 | 89.8 | 223.0 | 157.2 |
|   | 5 | 8.6 | 293.6 | 1.003 | 11.0 | 88.2 | 173.7 | 213.0 |
| Q | 1 | 6.7 | 112.9 | 1.011 | 25.8 | 80.2 | 94.9 | 37.9 |
|   | 4 | 6.8 | 88.2 | 1.013 | 17.5 | 20.1 | 38.2 | 14.1 |
|   | 5 | 5.8 | 53.0 | 1.008 | 12.4 | 13.4 | 26.1 | 11.8 |
| R | 1 | 6.9 | 40.0 | 1.004 | 13.8 | 35.5 | 60.6 | 33.8 |
|   | 4 | 7.5 | 41.0 | 1.004 | 7.0 | 17.3 | 33.3 | 24.6 |
|   | 5 | 8.6 | 26.1 | 1.001‡ | 5.2 | 19.7 | 27.8 | 17.5 |
| YY | 1 | 7.3 | 30.0 | 1.005 | 3.2** | 12.8* | 29.5 | 27.3 |
|   | 4 | 6.6 | 87.8 | 1.010 | 5.8 | 21.0 | 110.7 | 88.2 |
|   | 5 | 6.6 | 55.3 | 1.006 | 4.7** | 10.7 | 61.5 | 47.4 |
| CCC | 1 | 5.8 | 113.4 | 1.012 | 83.1 | 181.3 | 637.9 | 365.9 |
|   | 4 | 5.4 | 96.1 | 1.015 | 29.1 | 26.7 | 208.9 | 133.1 |
|   | 5 | 5.7 | 89.6 | 1.014 | 23.2 | 21.1 | 152.3 | 96.7 |
| III | 1 | 5.4 | 34.9 | 1.001‡ | 33.4 | 89.7 | 107.7 | 59.2 |
|   | 4 | 5.4 | 25.8 | 1.009 | 8.0 | 7.4 | 41.7 | 28.8 |
|   | 5 | 6.1 | 141.6 | 1.010 | 10.4 | 15.6 | 149.7 | 117.1 |

‡Indicates that the specimen validity criteria marked was not acceptable.
*Indicates that the ion ratio criteria were not met.
**Indicates that the value is below our established LOD/LOQ of 5 ng/mL and should be interpreted as a negative result.

TABLE 4

Sample Validity and Urine Results Summary at 20 mg/day (all metabolite data reported in ng/mL).

|  | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|
| Average | 6.52 | 113.61 | 1.01 | 18.38 | 43.67 | 102.39 | 60.97 |
| Standard Deviation | 1.03 | 72.35 | 0.01 | 23.16 | 68.39 | 108.52 | 70.37 |
| n | 53 | | | | | | |
| Maximum Value | 8.60 | 300.30 | 1.02 | 149.00 | 456.10 | 637.90 | 365.90 |
| Median Value | 6.50 | 95.30 | 1.01 | 12.45 | 22.90 | 60.60 | 34.25 |
| Minimum Value | 4.70 | 22.20 | 1.00 | 5.70 | 6.10 | 11.00 | 5.30 |

Samples that were deemed invalid based on pH and/or specific gravity (n=7) were not included in calculations. Any drug/metabolite concentration that was less than the LOD/LOQ (5 ng/mL) as noted in Table 3 was also excluded from the calculations.

Example 3

The urine of 12 patients who were prescribed 40 mg of Latuda® (lurasidone) was tested for compliance over 5 days (Table 5). The preponderance of M8/M9, M21, and M22 in the urine as the major metabolic urine compounds is shown in Table 5. Assuming 36 opportunities to determine the patient to be either positive or negative for Latuda® dosing, the use of M8/M9, M21, and M22 resulted in 100% correct identification of those taking the prescribed medicine. The data in Table 6 demonstrate the "normal" nature of the sample validity criteria (i.e., pH, specific gravity, and creatinine). Without the M8/M9, M21, or M22 metabolites, only ~92% were determined to be positive solely by the parent compound lurasidone. Thus, use of M8/M9, M21, and M22 as a urine biomarker at this dose adds value to compliance monitoring for Latuda®.

TABLE 5

Test Results from Patients Prescribed 40 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| S | 1 | 8.8 | 182.8 | 0.993‡ | 77.1 | 248.1 | 685.1 | 269.1 |
|   | 4 | 9.2‡ | 92.4 | 0.996‡ | 21.7 | 68.3 | 176.6 | 11.2 |
|   | 5 | 9.0‡ | 63.5 | 0.999‡ | 37.9 | 89.2 | 173.7 | 75.6 |
| T | 1 | 7.2 | 100.8 | 1.011 | 30.5 | 42.2 | 129.0 | 35.8 |
|   | 4 | 8.3 | 148.2 | 1.011 | 25.6 | 60.5 | 313.4 | 136.3 |
|   | 5 | 7.6 | 274.8 | 1.014 | 37.9 | 66.3 | 443.7 | 186.3 |
| U | 1 | 6.0 | 99.5 | 1.006 | 31.9 | 25.1 | 131.4 | 86.4 |
|   | 4 | 5.2 | 264.6 | 1.015 | 70.7 | 74.4 | 559.0 | 424.1 |
|   | 5 | 5.1 | 162.3 | 1.014 | 60.0 | 57.7 | 283.7 | 170.6 |
| V | 1 | 5.9 | 103.4 | 1.013 | 63.9 | 131.2 | 571.3 | 470.9 |
|   | 4 | 5.4 | 305.7 | 1.024 | 69.3 | 163.5 | 1282.8 | 1099.2 |
|   | 5 | 5.7 | 58.2 | 1.006 | 33.4 | 48.4 | 290.6 | 241.1 |
| W | 1 | 7.3 | 292.8 | 1.015 | 25.8 | 39.7 | 640.5 | 346.5 |
|   | 4 | 6.7 | 94.3 | 1.013 | 26.4 | 24.1 | 252.6 | 198.1 |
|   | 5 | 6.9 | 229.8 | 1.012 | 40.1 | 67.7 | 823.1 | 547.3 |
| X | 1 | 8.0 | 69.4 | 1.008 | 4.4** | 5.6 | 39.4 | 35.3 |
|   | 4 | 6.9 | 15.0‡ | 1.005 | 1.0** | 2.7** | 31.8 | 11.6 |
|   | 5 | 8.4 | 36.0 | 1.004 | 1.3** | 5.9 | 80.3 | 45.0 |
| Y | 1 | 5.8 | 77.5 | 1.011 | 30.6 | 53.4 | 201.5 | 140.3 |
|   | 4 | 5.4 | 201.7 | 1.021 | 41.3 | 59.0 | 373.8 | 291.5 |
|   | 5 | 7.3 | 72.7 | 1.009 | 35.8 | 38.9 | 112.5 | 104.7 |
| AA | 1 | 6.8 | 71.1 | 1.008 | 9.8 | 16.1 | 183.3 | 91.2 |
|   | 4 | 5.3 | 101.2 | 1.011 | 14.5 | 16.5 | 270.4 | 92.3 |
|   | 5 | 5.5 | 33.3 | 1.006 | 7.2 | 5.2 | 59.5 | 26.2 |
| BB | 1 | 5.9 | 217.1 | 1.016 | 112.1 | 155.1 | 345.6 | 151.7 |
|   | 4 | 7.2 | 47.3 | 1.004 | 54.0 | 66.4 | 66.4 | 48.7 |
|   | 5 | 5.6 | 206.0 | 1.018 | 192.1 | 220.1 | 525.9 | 220.7 |
| CC | 1 | 6.7 | 42.1 | 1.008 | 14.0 | 21.1 | 42.0 | 22.3 |
|   | 4 | 6.4 | 162.0 | 1.010 | 32.8 | 155.8 | 206.8 | 71.2 |
|   | 5 | 6.9 | 40.3 | 1.005 | 11.3 | 11.8 | 31.5 | 15.8 |
| DD | 1 | 6.2 | 45.9 | 1.006 | 11.8 | 17.2 | 53.2 | 11.5 |
|   | 4 | 7.5 | 71.1 | 1.007 | 12.8 | 10.9 | 59.2 | 14.0 |
|   | 5 | 7.1 | 133.9 | 1.010 | 7.8 | 11.5 | 101.3 | 26.7 |

TABLE 5-continued

Test Results from Patients Prescribed 40 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| DDD | 1 | 5.3 | 160.9 | 1.018 | 129.1 | 586.5 | 2766.0 | 2285.4 |
|  | 4 | 6.2 | 139.6 | 1.014 | 38.0 | 230.9 | 1164.2 | 1397.7 |
|  | 5 | 6.9 | 73.1 | 1.007 | 56.4 | 452.1 | 1010.8 | 1054.1 |

‡Indicates that the specimen validity criteria marked was not acceptable.
*Indicates that the ion ratio criteria were not met.
**Indicates that the value is below our established LOD/LOQ of 5 ng/mL and should be interpreted as a negative result.

TABLE 6

Sample Validity and Urine Results Summary at 40 mg/day (all metabolite data reported in ng/mL).

|  | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|
| Average | 6.50 | 129.27 | 1.01 | 44.23 | 91.90 | 407.47 | 306.08 |
| Standard Deviation | 0.92 | 80.21 | 0.005 | 39.43 | 126.81 | 529.54 | 480.90 |
| n | 33 |  |  |  |  |  |  |
| Maximum Value | 8.40 | 305.70 | 1.02 | 192.10 | 586.50 | 2766.00 | 2285.40 |
| Median Value | 6.70 | 101.00 | 1.01 | 33.10 | 50.90 | 252.60 | 136.30 |
| Minimum Value | 5.10 | 33.30 | 1.00 | 7.20 | 5.20 | 31.50 | 11.50 |

Samples that were deemed invalid based on pH and/or specific gravity (n=3) were not included in calculations. Any drug/metabolite concentration that was less than the LOD/LOQ (5 ng/mL) as noted in Table 5 was also excluded from the calculations.

Example 4

The urine of 2 patients who was prescribed 60 mg of Latuda® (lurasidone) was tested for compliance over 5 days (Table 7). The preponderance of M8/M9, M21, and M22 in the urine as the major metabolic urine compounds is shown in Table 7. Assuming 6 opportunities to determine the patient to be either positive or negative for Latuda® dosing, the use of M8/M9, M21, and M22 resulted in 100% correct identification of those taking the prescribed medicine. The data in Table 8 demonstrate the "normal" nature of the sample validity criteria (i.e., pH, specific gravity, and creatinine). Without the M8/M9, M21, or M22 metabolites, still 100% were determined to be positive solely by the parent compound lurasidone. Thus, use of M8/M9, M21, and M22 as a urine biomarker at this dose does not appear to add additional value to compliance monitoring for Latuda®.

TABLE 7

Test Results from Patients Prescribed 60 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| FF | 1 | 7.5 | 80.1 | 1.008 | 15.6 | 6.3 | 31.9 | 19.2 |
|  | 4 | 5.4 | 84.1 | 1.008 | 25.3 | 31.5 | 104.5 | 76.7 |
|  | 5 | 5.8 | 282.6 | 1.020 | 50.5 | 93.5 | 324.0 | 248.6 |
| GG | 1 | 5.6 | 37.2 | 1.010 | 16.3 | 24.6 | 112.5 | 85.0 |
|  | 4 | 5.2 | 122.1 | 1.015 | 36.8 | 50.1 | 260.3 | 199.8 |
|  | 5 | 5.8 | 151.0 | 1.013 | 37.3 | 55.3 | 279.1 | 266.7 |

‡Indicates that the specimen validity criteria marked was not acceptable.
*Indicates that the ion ratio criteria were not met.
**Indicates that the value is below our established LOD/LOQ of 5 ng/mL and should be interpreted as a negative result.

TABLE 8

Sample Validity and Urine Results Summary at 60 mg/day (all metabolite data reported in ng/mL).

|  | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
| --- | --- | --- | --- | --- | --- | --- | --- |
| Average | 5.88 | 126.18 | 1.01 | 30.30 | 43.55 | 185.38 | 149.33 |
| Standard Deviation | 0.75 | 78.43 | 0.004 | 12.49 | 27.59 | 107.25 | 93.56 |
| n | 6 |  |  |  |  |  |  |
| Maximum Value | 7.50 | 282.60 | 1.02 | 50.50 | 93.50 | 324.00 | 266.70 |
| Median Value | 5.70 | 103.10 | 1.01 | 31.05 | 40.80 | 186.40 | 142.40 |
| Minimum Value | 5.20 | 37.20 | 1.01 | 15.60 | 6.30 | 31.90 | 19.20 |

Example 5

The urine of 15 patients who were prescribed 80 mg of Latuda® (lurasidone) was tested for compliance over 5 days (Table 9). The preponderance of M8/M9, M21, and M22 in the urine as the major metabolic urine compounds is clearly demonstrated in Table 5. Assuming 45 opportunities to determine the patient to be either positive or negative for Latuda® dosing, the use of M8/M9, M21, and M22 resulted in ~96%% correct identification of those taking the prescribed medicine. The data in Table 10 demonstrate the "normal" nature of the sample validity criteria (i.e., pH, specific gravity, and creatinine). Without the M8/M9, M21, or M22 metabolites, only ~93% were determined to be positive solely by the parent compound lurasidone. Thus, use of M8/M9, M21, and M22 as a urine biomarker at this dose adds value to compliance monitoring for Latuda®.

TABLE 9

Test Results from Patients Prescribed 80 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
| --- | --- | --- | --- | --- | --- | --- | --- | --- |
| HH | 1 | 6.2 | 127.3 | 1.016 | 138.5 | 400.4 | 1839.9 | 831.6 |
|  | 4 | 6.3 | 205.1 | 1.013 | 83.8 | 192.9 | 1954.6 | 805.5 |
|  | 5 | 7.6 | 87.4 | 1.008 | 67.6 | 118.0 | 555.0 | 388.1 |
| II | 1 | 5.5 | 102.7 | 1.013 | 147.1 | 258.8 | 1613.9 | 736.5 |
|  | 4 | 5.9 | 155.9 | 1.017 | 144.8 | 195.5 | 2289.0 | 804.5 |
|  | 5 | 7.4 | 148.7 | 1.012 | 112.7 | 117.2 | 1475.2 | 773.7 |
| JJ | 1 | 6.1 | 218.7 | 1.011 | 57.3 | 29.9 | 309.4 | 129.2 |
|  | 4 | 6.7 | 281.9 | 1.009 | 69.6 | 142.8 | 1163.8 | 909.3 |
|  | 5 | 5.9 | 315.9 | 1.012 | 100.6 | 243.3 | 1615.3 | 1134.8 |
| KK | 1 | 5.3 | 147.4 | 1.013 | 152.8 | 343.3 | 1274.9 | 795.7 |
|  | 4 | 6.1 | 130.9 | 1.011 | 83.3 | 135.3 | 662.1 | 575.0 |
|  | 5 | 5.0 | 290.2 | 1.020 | 72.4 | 121.0 | 1379.3 | 773.0 |
| LL | 1 | 5.7 | 247.7 | 1.013 | 556.6 | 897.1 | 7993.3 | 2285.6 |
|  | 4 | 5.3 | 218.2 | 1.016 | 503.8 | 695.0 | 6790.7 | 1949.3 |
|  | 5 | 6.5 | 160.8 | 1.009 | 264.0 | 276.7 | 4321.1 | 1709.6 |
| MM | 1 | 6.9 | 191.0 | 1.011 | 175.2 | 377.1 | 2054.5 | 1152.6 |
|  | 4 | 7.1 | 158.7 | 1.010 | 96.4 | 152.9 | 836.2 | 679.7 |
|  | 5 | 6.1 | 301.5 | 1.015 | 116.3 | 162.6 | 1663.1 | 1009.9 |
| NN | 1 | 6.9 | 74.4 | 1.007 | 52.6 | 66.3 | 329.0 | 91.8 |
|  | 4 | 7.7 | 90.8 | 1.007 | 43.7 | 54.6 | 293.8 | 102.0 |
|  | 5 | 7.7 | 88.7 | 1.006 | 38.9 | 53.2 | 288.5 | 107.9 |
| VV | 1 | 8.7 | 124.2 | 1.009 | 23.0 | 58.5 | 210.5 | 171.0 |
|  | 4 | 7.9 | 203.3 | 1.011 | 0.1** | 0.0** | 0.0** | 0.0** |
|  | 5 | 6.6 | 249.6 | 1.010 | 36.7 | 146.4 | 448.8 | 387.6 |
| WW | 1 | 8.1 | 230.7 | 1.008 | 40.5 | 272.2 | 1014.4 | 2176.4 |
|  | 4 | 5.3 | 171.3 | 1.016 | 162.5 | 202.2 | 1214.3 | 1053.3 |
|  | 5 | 7.1 | 127.5 | 1.010 | 48.3 | 80.5 | 534.6 | 886.9 |
| EEE | 1 | 7.0 | 17.9 | 1.002 | 10.1 | 18.2 | 29.0 | 15.1 |
|  | 4 | 5.5 | 36.3 | 1.003 | 14.5 | 15.4 | 32.6 | 28.2 |
|  | 5 | 5.7 | 124.7 | 1.007 | 41.0 | 42.2 | 69.8 | 88.4 |
| FFF | 1 | 7.0 | 137.4 | 1.011 | 210.7 | 380.1 | 1469.5 | 564.9 |
|  | 4 | 5.5 | 148.1 | 1.014 | 70.4 | 82.1 | 913.3 | 349.3 |
|  | 5 | 5.5 | 20.9 | 1.003 | 16.1 | 11.8 | 104.9 | 54.4 |
| HHH | 1 | 6.4 | 285.5 | 1.010 | 145.2 | 290.9 | 8565.0 | 6401.5 |
|  | 4 | 6.5 | 235.3 | 1.012 | 298.3 | 837.0 | 9603.9 | 5431.7 |
|  | 5 | 6.6 | 222.5 | 1.013 | 539.5 | 887.1 | 9292.5 | 4613.8 |

TABLE 9-continued

Test Results from Patients Prescribed 80 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| JJJ | 1 | 6.9 | 83.2 | 1.007 | 59.5 | 88.0 | 443.6 | 320.0 |
|  | 4 | 5.5 | 187.7 | 1.014 | 35.9 | 14.3 | 199.5 | 84.7 |
|  | 5 | 7.3 | 141.1 | 1.012 | 69.5 | 71.2 | 1236.1 | 398.7 |
| KKK | 1 | 7.3 | 355.5 | 1.009 | 4.8** | 3.3* ** | 48.4 | 40.7 |
|  | 4 | 6.6 | 18.3 | 1.003 | 52.0 | 147.2 | 462.7 | 476.7 |
|  | 5 | 7.4 | 43.7 | 1.007 | 22.9 | 30.3 | 142.1 | 243.7 |
| LLL | 1 | 5.7 | 299.7 | 1.020 | 0.0** | 0.0** | 0.0** | 0.0** |
|  | 4 | 5.5 | 248.0 | 1.019 | 32.9 | 246.2 | 915.3 | 1120.9 |
|  | 5 | 5.6 | 306.3 | 1.023 | 43.5 | 295.6 | 1277.9 | 1502.4 |

‡Indicates that the specimen validity criteria marked was not acceptable.
*Indicates that the ion ratio criteria were not met.
**Indicates that the value is below our established LOD/LOQ of 5 ng/mL and should be interpreted as a negative result.

TABLE 10

Sample Validity and Urine Results Summary at 80 mg/day (all metabolite data reported in ng/mL).

|  | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|
| Average | 6.47 | 172.50 | 1.01 | 120.26 | 220.27 | 1835.61 | 1026.87 |
| Standard Deviation | 0.88 | 87.12 | 0.005 | 131.50 | 226.06 | 2550.78 | 1359.91 |
| n | 45 |  |  |  |  |  |  |
| Maximum Value | 8.70 | 355.50 | 1.02 | 556.60 | 897.10 | 9603.90 | 6401.50 |
| Median Value | 6.50 | 158.70 | 1.01 | 70.00 | 146.80 | 1014.40 | 736.50 |
| Minimum Value | 5.00 | 17.90 | 1.00 | 10.10 | 11.80 | 29.00 | 15.10 |

Any drug/metabolite concentration that was less than the LOD/LOQ (5 ng/mL) as noted in Table 5 was also excluded from the calculations.

Example 6

The urine of 1 patient who was prescribed 100 mg of Latuda® (lurasidone) was tested for compliance over 5 days (Table 11). The preponderance of M8/M9, M21, and M22 in the urine as the major metabolic urine compounds is clearly demonstrated in Table 11. Assuming 3 opportunities to determine the patient to be either positive or negative for Latuda® dosing, the use of M8/M9, M21, and M22 resulted in 100% correct identification of those taking the prescribed medicine. The data in Table 12 demonstrate the "normal" nature of the sample validity criteria (i.e., pH, specific gravity, and creatinine). Without the M8/M9, M21, or M22 metabolites, still 100% were determined to be positive solely by the parent compound lurasidone.

TABLE 11

Test Results from Patients Prescribed 100 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| OO | 1 | 5.6 | 172.4 | 1.014 | 94.9 | 188.4 | 1404.7 | 271.2 |
|  | 4 | 5.9 | 239.9 | 1.012 | 62.5 | 186.4 | 1599.4 | 456.6 |
|  | 5 | 6.0 | 141.9 | 1.011 | 64.5 | 153.9 | 1032.3 | 253.8 |

‡Indicates that the specimen validity criteria marked was not acceptable.
*Indicates that the ion ratio criteria were not met.
**Indicates that the value is below our established LOD/LOQ of 5 ng/mL and should be interpreted as a negative result.

TABLE 12

Sample Validity and Urine Results Summary at 100 mg/day (all metabolite data reported in ng/mL).

| | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|
| Average | 5.83 | 184.73 | 1.01 | 73.97 | 176.23 | 1345.47 | 327.20 |
| Standard Deviation | 0.17 | 40.95 | 0.00 | 14.82 | 15.81 | 235.28 | 91.77 |
| n | 3 | | | | | | |
| Maximum Value | 6.00 | 239.90 | 1.01 | 94.90 | 188.40 | 1599.40 | 456.60 |
| Median Value | 5.90 | 172.40 | 1.01 | 64.50 | 186.40 | 1404.70 | 271.20 |
| Minimum Value | 5.60 | 141.90 | 1.01 | 62.50 | 153.90 | 1032.30 | 253.80 |

Example 7

The urine of 6 patients who were prescribed 120 mg of Latuda® (lurasidone) was tested for compliance over 5 days (Table 13). The preponderance of M8/M9, M21, and M22 in the urine as the major metabolic urine compounds is clearly demonstrated in Table 13. Assuming 18 opportunities to determine the patient to be either positive or negative for Latuda® dosing, the use of M8/M9, M21, and M22 resulted in 100% correct identification of those taking the prescribed medicine. The data in Table 14 demonstrate the "normal" nature of the sample validity criteria (i.e., pH, specific gravity, and creatinine). Without the M8/M9, M21, or M22 metabolites, 100% were still determined to be positive solely by the parent compound lurasidone.

TABLE 13

Test Results from Patients Prescribed 120 mg/day Latuda ® (all metabolite data reported in ng/mL).

| Subject | Day | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|---|
| PP | 1 | 7.6 | 90.6 | 1.008 | 102.7 | 185.5 | 506.6 | 315.2 |
| | 4 | 8.0 | 106.5 | 1.007 | 87.3 | 89.0 | 359.6 | 296.1 |
| | 5 | 7.7 | 57.1 | 1.008 | 59.1 | 63.4 | 491.2 | 436.1 |
| QQ | 1 | 6.7 | 13.9‡ | 1.002 | 21.7 | 17.1 | 150.3 | 50.4 |
| | 4 | 6.7 | 26.5 | 1.001‡ | 23.7 | 17.4 | 207.0 | 75.2 |
| | 5 | 6.1 | 129.7 | 1.007 | 61.6 | 56.7 | 708.6 | 273.6 |
| RR | 1 | 6.1 | 230.4 | 1.019 | 83.9 | 329.9 | 2127.9 | 1608.2 |
| | 4 | 6.9 | 141.5 | 1.008 | 46.4 | 269.8 | 2039.4 | 1590.1 |
| | 5 | 6.7 | 149.7 | 1.010 | 63.3 | 313.7 | 2507.7 | 1697.6 |
| SS | 1 | 7.7 | 24.5 | 1.003 | 126.2 | 130.2 | 413.7 | 262.9 |
| | 4 | 7.4 | 37.9 | 1.004 | 150.7 | 124.9 | 731.4 | 340.2 |
| | 5 | 7.1 | 69.1 | 1.009 | 251.7 | 208.1 | 1588.9 | 620.5 |
| UU | 1 | 5.3 | 180.6 | 1.016 | 23.4 | 170.9 | 425.0 | 305.7 |
| | 4 | 5.2 | 217.1 | 1.018 | 27.5 | 23.1 | 202.4 | 207.5 |
| | 5 | 5.5 | 110.7 | 1.013 | 12.4 | 7.8 | 81.6 | 75.7 |
| GGG | 1 | 6.3 | 40.2 | 1.002 | 148.7 | 162.4 | 1094.9 | 774.5 |
| | 4 | 6.0 | 303.7 | 1.014 | 260.1 | 586.3 | 6580.7 | 4807.4 |
| | 5 | 6.6 | 16.5‡ | 1.001‡ | 57.2 | 50.3 | 244.9 | 224.4 |

‡Indicates that the specimen validity criteria marked was not acceptable.
*Indicates that the ion ratio criteria were not met.
**Indicates that the value is below our established LOD/LOQ of 5 ng/mL and should be interpreted as a negative result.

TABLE 14

Sample Validity and Urine Results Summary at 120 mg/day (all metabolite data reported in ng/mL).

| | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|
| Average | 6.64 | 125.95 | 1.01 | 95.42 | 171.18 | 1250.62 | 853.86 |
| Standard | 0.87 | 77.40 | 0.01 | 73.60 | 145.10 | 1562.57 | 1151.33 |

TABLE 14-continued

Sample Validity and Urine Results Summary at 120 mg/day (all metabolite data reported in ng/mL).

|  | pH | Creatinine (mg/dL) | Specific Gravity | Lurasidone | Hydroxy-Lurasidone (M8/M9) | S-Methyl Lurasidone (M21) | S-Methyl Hydroxy Lurasidone (M22) |
|---|---|---|---|---|---|---|---|
| Deviation |  |  |  |  |  |  |  |
| n | 16 |  |  |  |  |  |  |
| Maximum Value | 8.00 | 303.70 | 1.02 | 260.10 | 586.30 | 6580.70 | 4807.40 |
| Median Value | 6.70 | 110.70 | 1.01 | 73.60 | 146.30 | 607.60 | 327.70 |
| Minimum Value | 5.20 | 24.50 | 1.00 | 12.40 | 7.80 | 81.60 | 50.40 |

Samples that were deemed invalid based on pH and/or specific gravity (n=2) were not included in calculations.

These examples demonstrate that lurasidone metabolites M8/M9, M21, and M22 provide a greater level of sensitivity and consistency among subjects on lurasidone therapy than afforded by the parent drug alone, particularly at lower doses, and therefore provide superior urine analytes for evaluation of a subject's compliance with a lurasidone therapeutic regimen.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A method for identifying a subject as non-compliant with a prescribed lurasidone therapy, the method comprising:
   obtaining a fluid sample from a subject who has been prescribed lurasidone therapy;
   determining a level of M8/M9, M21, and/or M22 in the fluid sample; and
   identifying the subject as adherent to the prescribed lurasidone therapy if the fluid sample contains M8/M9, M21, and/or M22 above a threshold level but non-adherent if the fluid sample contains no M8/M9, M21, and/or M22 or an amount of M8/M9, M21, and/or M22 below a threshold level,
   wherein the fluid sample is a urine sample, and
   wherein the step of determining the level of the M8/M9, M21, and/or M22 in the fluid sample comprises mass spectrometry.

2. The method of claim 1 further comprising counseling the subject on dangers of non-adherence to lurasidone therapy if the subject is identified as non-adherent.

3. The method of claim 1, wherein the threshold level is a minimum detectable amount of M8/M9, M21, and/or M22.

4. The method of claim 1, wherein the threshold level is about 50 ng/mL.

5. The method of claim 1, wherein the threshold level is about 5 ng/mL.

6. A method for identifying a subject as non-compliant with a prescribed lurasidone therapy, the method comprising:
   obtaining a fluid sample from a subject who has been prescribed lurasidone therapy;
   determining a level of at least two of M8/M9, M21, and M22 in the fluid sample; and
   identifying the subject as adherent to the prescribed lurasidone therapy if the fluid sample contains the at least two of M8/M9, M21, and M22 above a threshold level but non-adherent if the fluid sample contains no amount of the at least two of M8/M9, M21, and M22 or an amount of the at least two of M8/M9, M21, and M22 below a threshold level,
   wherein the fluid sample is a urine sample, and
   wherein the step of determining the level of the at least two of M8/M9, M21, and M22 in the fluid sample comprises mass spectrometry.

7. The method of claim 6, wherein the threshold level is a minimum detectable amount of M8/M9, M21, and/or M22.

8. The method of claim 6, wherein the threshold level is about 50 ng/mL.

9. The method of claim 6, wherein the threshold level is about 5 ng/mL.

10. The method of claim 6, wherein the at least two of M8/M9, M21, and M22 comprises M8/M9 and M21.

11. The method of claim 6, wherein the at least two of M8/M9, M21, and M22 comprises M8/M9 and M22.

12. The method of claim 6, wherein the at least two of M8/M9, M21, and M22 comprises M21 and M22.

13. The method of claim 6, wherein the at least two of M8/M9, M21, and M22 comprises M8/M9, M21 and M22.

14. A method for identifying a subject as non-compliant with a prescribed lurasidone therapy, the method comprising:
   obtaining a fluid sample from a subject who has been prescribed lurasidone therapy;
   determining a level of M8/M9, M21, and M22 in the fluid sample; and
   identifying the subject as adherent to the prescribed lurasidone therapy if the fluid sample contains M8/M9, M21, and M22 above a threshold level but non-adherent if the fluid sample contains no amount of M8/M9, M21, or M22 or an amount of M8/M9, M21, and M22 below a threshold level,
   wherein the fluid sample is a urine sample, and
   wherein the step of determining the level of M8/M9, M21, and M22 in the fluid sample comprises mass spectrometry.

15. The method of claim 14, wherein the threshold level is a minimum detectable amount of M8/M9, M21, and/or M22.

16. The method of claim 14, wherein the threshold level is about 50 ng/mL.

17. The method of claim 14, wherein the threshold level is about 5 ng/mL.

* * * * *